United States Patent [19]

Nelson

[11] 4,177,346

[45] Dec. 4, 1979

[54] 1,5-DISUBSTITUTED-2-PYRROLIDONES

[75] Inventor: Albin J. Nelson, Westchester, N.Y.

[73] Assignee: Pfizer Inc., New York, N.Y.

[21] Appl. No.: 885,908

[22] Filed: Mar. 13, 1978

Related U.S. Application Data

[63] Continuation-in-part of Ser. No. 712,362, Aug. 6, 1976, abandoned.

[51] Int. Cl.$^2$ .................. C07D 207/00; C07D 403/06
[52] U.S. Cl. ................................ 542/427; 542/416; 542/420; 542/442; 542/444; 542/432; 542/433; 260/326.43; 260/326.45; 260/326.5 FL; 260/326.35; 544/105; 548/253
[58] Field of Search ............... 542/400, 413, 476, 426, 542/429, 420, 427, 416, 442, 444, 432, 433; 260/326.43, 326.45, 308 D, 326.5 FL, 326.35; 544/105

[56] References Cited

U.S. PATENT DOCUMENTS

| | | | |
|---|---|---|---|
| 3,117,975 | 1/1964 | Bortneck et al. | 260/326.45 X |
| 3,954,741 | 5/1976 | Schaaf et al. | 542/426 X |
| 3,975,399 | 8/1976 | DeFranco et al. | 260/326.43 X |
| 3,984,400 | 10/1976 | Eggler et al. | 542/429 X |
| 3,994,956 | 11/1976 | Morozowich | 260/395 X |

OTHER PUBLICATIONS

Harrison et al., "Synthesis of 11-Thiaprostaglandins", in Tetrahedron Ltrs., No. 13, pp. 1165–1168, 1975.

*Primary Examiner*—Arthur P. Demers
*Attorney, Agent, or Firm*—Connolly and Hutz

[57] ABSTRACT

A series of 1,5-disubstituted-2-pyrrolidones which are prostaglandin-like in character and the processes for making them are disclosed.

15 Claims, No Drawings

1,5-DISUBSTITUTED-2-PYRROLIDONES

CROSS REFERENCE TO RELATED APPLICATIONS

This application is a continuation in part of application Ser. No. 712,362 filed Aug. 6, 1976, now abandoned.

BACKGROUND OF THE INVENTION

This invention relates to a novel series of 1,5-disubstituted-2-pyrrolidones which are prostaglandin-like in chemical structure and biological character, the process for making such 2-pyrrolidones and synthetic intermediates employed in these processes.

The $C_{20}$ unsaturated fatty acids, known as prostaglandins, form a large family of naturally-occurring compounds. These molecules may have as many as fine asymmetric centers and are present in and evoke response from a diversity of biological tissues. An example of a particular species of the prostaglandin E genera is $PGE_2$ pictured below.

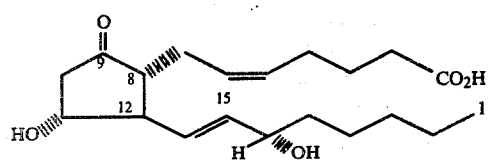

prostaglandin $E_2$

According to the notation usually employed to describe the stereochemistry of prostaglandins, a heavy solid line represents the β configuration which is defined as a bond coming up out of the plane of the paper and toward the reader. In a like manner, a dotted or hashed line represents the α configuration which is defined as a bond goin behind the plane of the paper and away from the reader. Thus, the configuration of the prostaglandin $E_2$, pictured above, is α at carbon 8 and β at carbon 12. [S. Bergstrom, et al., Acta. Chem. Scand., 16, 501 (1962)].

By the same terminology, a wavy line represents a mixture of the two forms α and β. Thus, a 2-pyrrolidone of the structure:

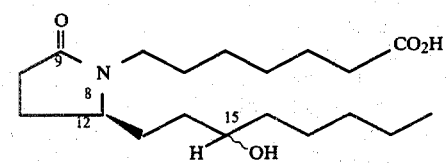

represents a mixture of the epimers

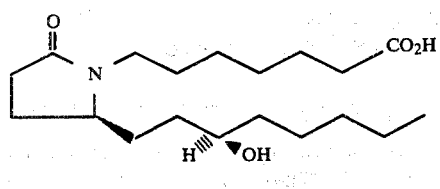

and

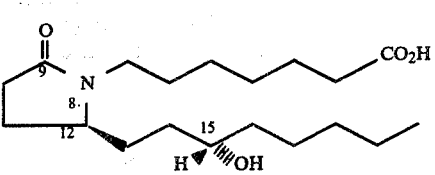

By reference to the pyrrolidone of structure II and prostaglandin $E_2$ shown above, a stereochemical comparison can be made between the two sets of compounds. The stereochemistry at positions 12 and 15 is the same in both types but that at position 8 is different. That is, the configuration of the C8-C7 bond of the prostaglandin E is α, but that of the N8-C7 bond is in the plane of the paper according to the representation of the drawing above. Another way to represent the above two examples which will develop a better appreciation of this difference in configuration is the edge-on drawing below:

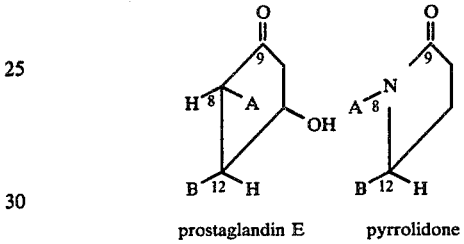

prostaglandin E    pyrrolidone where A and B stand for the two side chains of the examples. Here the illustration depicts the eclipsing of the A-C8 bond with the C12-H bond and the eclipsing of the C12-B bond with the C8-H bond in the case of the prostaglandin E and the bisecting position of the A-N8 bond with respect to the dihedral angle formed by B-C12-H in the case of the pyrrolidone. This difference in conformation is a result of the planarity generated by the amide moiety of the pyrrolidone. ["Basic Principles of Organic Chemistry", J. D. Roberts and M. C. Caserio, W. A. Benjamin, New York, 1965, p. 674]

A systematic name for a 1,5-disubstituted-2-pyrrolidone of the structure:

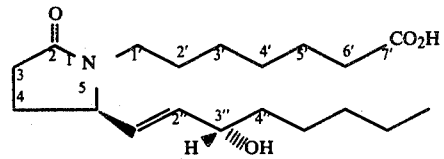

is 1-(6'-carboxyhexyl)-5β-(3"α-hydroxyoct-1"-enyl)-2-pyrrolidone and it also can be named as a derivative of 11-desoxyprostaglandin $E_1$; that is, 8-aza-11-desoxy $PGE_1$.

The corresponding 8-aza-11-desoxy $PGE_2$ compound has the structure:

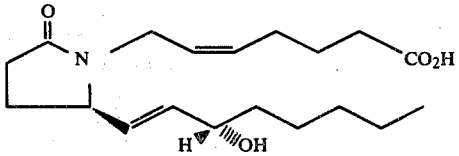

where the single bond between C2' and C3' has been replaced by a double bond. The corresponding 8-aza-11-desoxy PGE₀ compound has the structure:

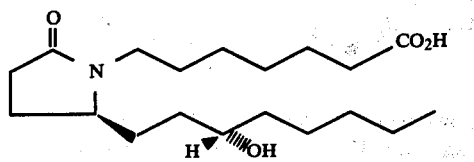

where the double bond between C1" and C2" has been replaced by a single bond.

The above pyrrolidones have several centers of asymmetry, and can exist in the racemic (optically inactive) form and in either of the two enantiomeric (optically active) forms, i.e. the dextrorotatory (D) and levorotatory (L) forms. As drawn above, each pyrrolidone structure represents the particular active form or enantiomer which is derivable in part from D-glutamic acid. The mirror image or optical antipode of each of the above structures represents the other enantiomer of that pyrrolidone and is derivable in part from L-glutamic acid.

For instance, the optical antipode of 1-(6'-carboxyhexyl)-5β-(3"α-hydroxyoct-1"-enyl)-2-pyrrolidone is drawn as:

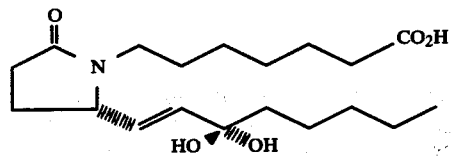

and is called 1-(6'-carboxyhexyl)-5α-(3"β-hydroxyoct-1"-enyl)-2-pyrrolidone.

As pointed out earlier, substitution of a nitrogen for the carbon at C8 causes a dramatic change in the three dimensional conformation of the resultant prostaglandin. Because structure is related to biological activity and often a subtle change in structure such as a conformational change will have a profound effect upon the biological activity, such molecular modification of prostaglandins by substitution of heteroatoms has been investigated recently. Most compounds are attempts at investigation of heteroatom substitutions at the C9 and C11 prostaglandin positions and include such examples as 9-oxaprostaglandins (I. Vlattas, Tetrahedron Let., 4455 (1974)]; 11-oxaprostaglandins [A. Fougerousse, Tetrahedron Let., 3983 (1974)] and S. Hanessian et al., Tetrahedron Let., 3983 (1974) and 9-thiaprostaglandins [I. Vlattas, Tetrahedron, Let., 4459 (1974)].

Two 8-aza-11-desoxy prostaglandin E's with the natural ω-side chain, that is, compounds with the aza substitution at C8 of 11-desoxy prostaglandin E₁ and E₂ have also been reported in the literature [G. Bolliger and J. M. Muchowski, Tetrahedron Let., 2931 (1975) (Aug. 1975); and J. W. Bruin, et al., Tetrahedron Let., 4599 (1975)]. These examples of pyrrolidone compounds are outside of the scope of the present invention which presents a higher order of complexity and molecular variation at the C1 prostaglandin position and in the ω-side chain. Relatively little biological activity is reported for these literature examples and they can be contrasted in form and in molecular complexity with the novel compounds of the present invention.

The natural prostaglandins and many of their derivatives such as the esters, acylates, and pharmacologically acceptable salts, are extremely potent inducers of various biological responses [D. E. Wilson, Arch. Intern. Med., 133 (29) (1974)] in tissues composed of smooth muscle such as those of the cardiovascular, pulmonary, gastrointestinal and reproductive systems, in cellular tissues such as those of the central nervous, hematologic, reproductive, gastrointestinal, pulmonary, nephritic, epidermal, cardiovascular and adipose systems and also operate as mediators in the process of homeostasis. With such a wide range of responses, it is apparent that the prostaglandins are involved in basic biological processes of the cell. Indeed, this basic implication of prostaglandins is supported by the fact that they can be found in cellular tissue of almost all animal organisms.

Often on such a cellular level the actions of closely related natural prostaglandins may be opposite. For instance, the effect of PGE₂ on human platelets is enhancement of aggregation while that of PGE₁ is inhibition of aggregation.

Such contrasting effects may also be observed at the tissue level. For instance, in vivo PGE₂ action on the cardiovascular system of mammals manifests itself by causing hypotension while the in vivo action of PGF₂α is hypertension [J. B. Lee, Arch. Intern. Med., 133 56 (1974)]. However, the ability to predict the biological action of prostaglandin classes based upon such observations is largely illusory at present. For instance, while the cardiovascular actions of PGE₂ and PGF₂α are opposite as described above, their in vivo or in vitro action on mammalian uterine smooth muscle is the same and is stimulatory (causes contraction) [H. R. Behrman, et al., Arch. Intern. Med., 133 77 (1974)].

In the preparation of synthetic pharmaceutical agents, among the principal objects is the development of compounds which are highly selective in their pharmacological activity and which have an increased duration of activity over their naturally occurring relatives. In a series of compounds which is similar to the naturally-occurring prostaglandins, increasing selectivity of a single compound usually involves the enhancement of one prostaglandin-like physiological effect and the diminution of the others. By increasing the selectivity, one would alleviate the severe side effects frequently observed following administration of the natural prostaglandins; for example, those gastrointestinal side effects of diarrhea and emesis or cardiovascular side effects when bronchodilator effects are desired. Recent developments directed toward an increase of biological selectivity include the 11-desoxy prostaglandins [N. H. Anderson, Arch. Intern. Med., 133, 30 (1974) Review], 2-descarboxy-2-(tetrazol-5-yl)-11-desoxy-15-substituted-ω-pentanorprostaglandins (M. R. Johnson et al., U.S. Pat. No. 3,932,389) where certain modifications are cited as producing selective vasodilator, antiulcer, antifertility, bronchodilator and antihypertensive properties, 16-phenoxy-16-ω-tetranor prostaglandins having antifertility activity (U.K. Pat. No. 1,350,971) and 1-imide and 1-sulfonimide prostaglandins (U.S. Pat. No. 3,954,741).

SUMMARY OF THE INVENTION

The present invention comprises prostaglandin-like compounds which have selective and potent biological activity and which have the structure:

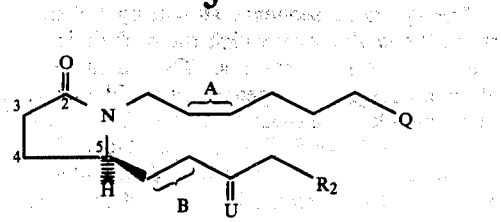

wherein:
Q is selected from the group consisting of

tetrazol-5-yl and

A is a single or cis double bond;
B is a single or trans double bond;
U is H▼''''/OH, HO▼''''/H or HO∼H;
$R_2$ is selected from the group consisting of α-thienyl, phenyl, phenoxy, monosubstituted phenyl and monosubstituted phenoxy, said substitutents being selected from the group consisting of chloro, fluoro, phenyl, methoxy, trifluoromethyl and alkyl having from one to three carbon atoms;
$R_3$ is selected from the group consisting of hydrogen, alkyl having from one to five carbon atoms, phenyl and p-biphenyl;
$R_4$ is selected from the group consisting of

and $-SO_2R_5$, said $R_5$ being selected from the group consisting of phenyl and alkyl having from one to five carbon atoms;
or the alkali, alkaline earth or ammonium salts of those compounds having a carboxylate or tetrazol-5-yl group.

In addition the present invention comprises intermediates which will allow the preparation of the final products above and which have the structures:

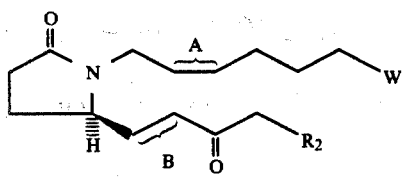

wherein W is selected from the group consiting of

tetrazol-5-yl, N-(acyloxymethyl)tetrazol-5-yl having from two to five carbon atoms in the acyloxy group, N-(phthalidyl)tetrazol-5-yl and N-(tetrahydropyran-2-yl)tetrazol-5-yl, and A, B, $R_2$ and $R_3$ are each defined as above;

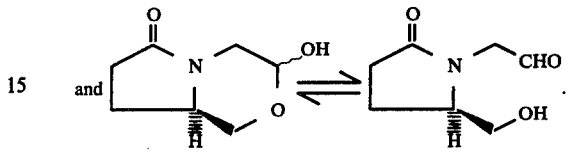

wherein W and A are defined as above;

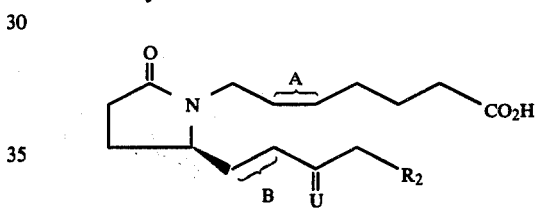

Two interesting series of 8-azaprostaglandins of the present invention are those with aryl and with aryloxy substituents at the $R_2$ position. The α-thienyl, phenyl and substituted phenyl compounds display selective hypotensive activity and good antisecretory activity while the phenoxy and substituted phenoxy compounds display good antisecretory activity and low hypotensive activity.

An especially interesting series of compounds is represented by the structure

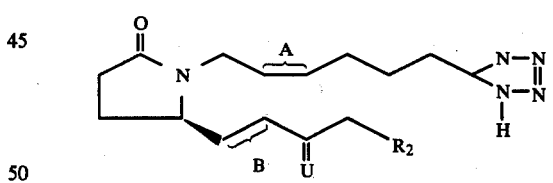

wherein A, B, U and $R_2$ are defined as above.
Another especially interesting series of compounds which have selective biological activity is represented by the structure:

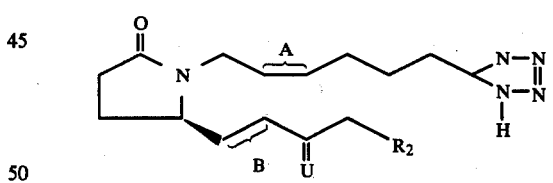

wherein A, B, U and $R_2$ are defined as above.
Especially preferred for their selective biological activity are:
1-(6'-carboxyhexyl)-5β-(3''α-hydroxy-4''-phenylbut-1''-enyl)-2-pyrrolidone and the methyl ester,
1-(6'-carboxy-hex-2'-enyl)-5β-(3''α-hydroxy-4''-phenylbut-1''-enyl)-2-pyrrolidone,
1-(6'-carboxyhexyl)-5β-(3''α-hydroxy-4''-phenoxybut-1''-enyl)-2-pyrrolidone,
1-(6'-carboxyhex-2'-enyl)-5β-(3''α-hydroxy-4''-phenoxybut-1''-enyl)-2-pyrrolidone,
1-(6'-carboxyhexyl)-5β-(3''α-hydroxy-4''-phenoxybutanyl)-2-pyrrolidone,
the compounds wherein 6'-(tetrazol-5-yl) replaces the 6'-carboxy group of each of the above especially preferred compounds, and the compounds wherein a 3"β-hydroxy replaces the 3"α-hydroxy group of each of the above 6'-carboxy and 6'-(tetrazol-5-yl) compounds.

DETAILED DESCRIPTION OF THE INVENTION

The pyrrolidone compounds of the present invention of prostamimetics are prepared in an optically active form by six step sequence which attaches the two side chains, the α or top side chain and the ω or bottom side chain, to the pyrrolidone ring and starts with a resolved amino acid, D-glutamic acid. The use of the D-glutamic acid establishes the absolute conformation of the C5 of the 2-pyrrolidone ring and pre-empts the necessity of resolving this position at the end of the synthesis.

The synthetic sequence shown by Scheme A illustrates the methods by which the α chain is attached to the 2-pyrrolidone nucleus. The methods described allow preparation of a generic pyrrolidone intermediate 19 having variable functionality at the C7' position and at the C2'-C3' bond. The final products of the present invention are then synthesized from intermediate 19 according to the methods presented in Schemes B, C and D.

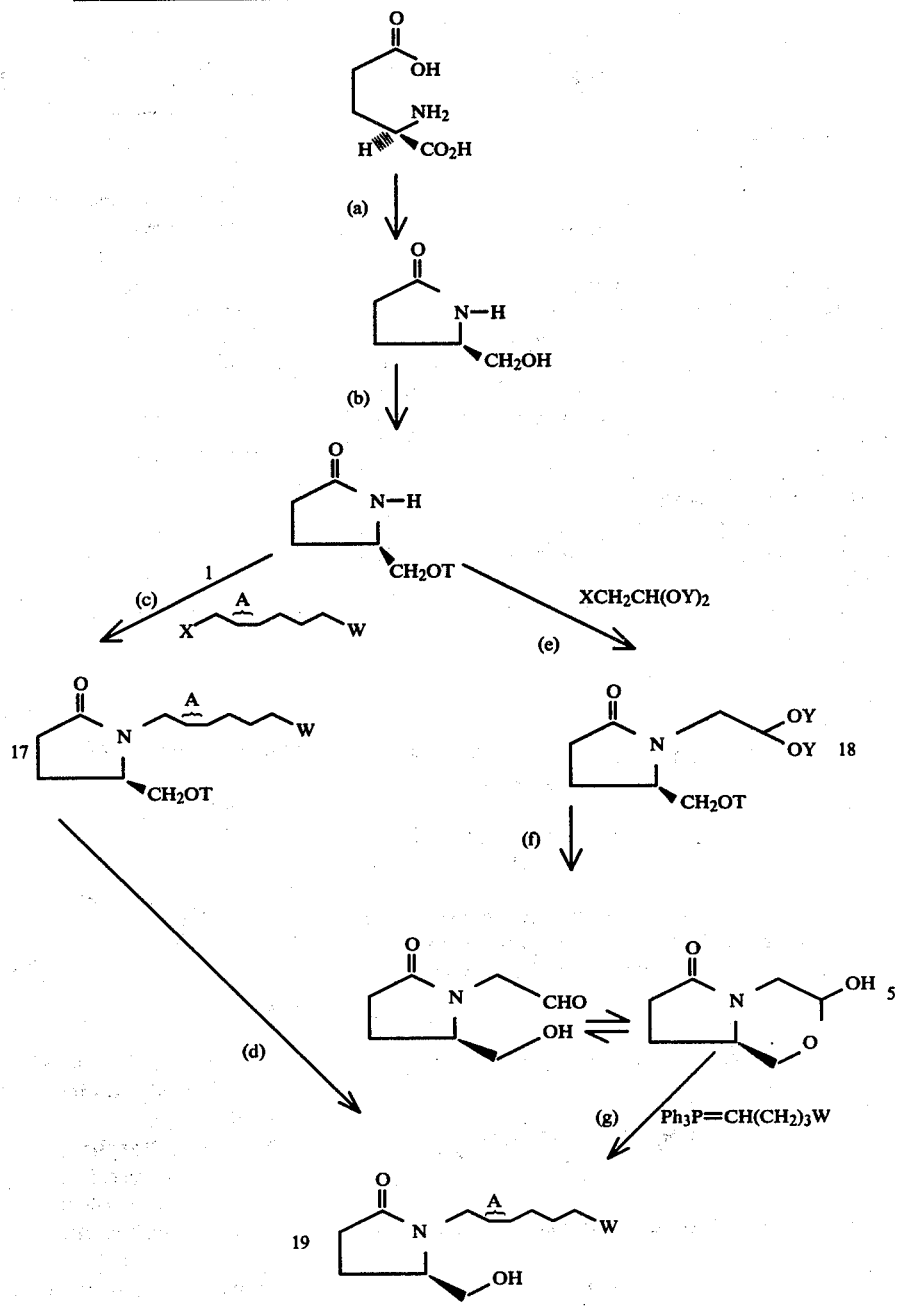

A brief summary of the steps in Scheme A is as follows. The first step, marked (a), illustrating the cyclization of D-glutamic acid to methyl D-pyroglutamate and the reduction of the pyroglutamate to 5-D-hydroxy-2-pyrrolidone is known [V. Bruckner et al., *Acta. Chim. Hung. Tomus*, 21, 106 (1959)]. The second step (b) is the protection of the hydroxymethyl group with protecting agent T which can be any group suitable for the protection of the hydroxyl against alkylation; for instance, benzyl, dimethyl-t-butyl silyl, acetyl 1-ethoxyethyl, or especially tetrahydropyranyl. Steps (c) and (e) illustrate the alkylation of the sodium or lithium salt of pyrrolidone 1 by alkylating agents of the formula

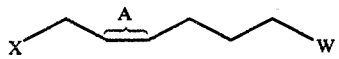

or XCH₂CH(OY)₂, respectively, wherein X is Cl, I, or especially Br; W is CO₂R₃, N-acyloxymethyl)tetrazol-5-yl having from two to five carbon atoms in the acyloxy group, N-(phthalidyl)tetrazol-5-yl, N-(tetrahydropyran-2-yl) tetrazol-5-yl or tetrazol-5-yl; Y is alkyl having from one to three carbon atoms, and A and R₃ are defined as above. Step (d) is the removal of protecting group T, the method of which will depend upon the identity of T. Step (f) is the deprotection of the pyrrolidone compound 18 to produce in situ 1-(ethan-2'-al)-5-hycroxymethyl-2-pyrrolidone which can exist in intimate equilibrium with the hemi-acetal compound 5. Step (g) is a Wittig reaction of the equilibrium mixture containing bicylco [4,3,0]nonan-5-one 5 with a phosphorane of the structure Ph₃P=CH(CH₂)₃W wherein W, defined above, is unprotected to produce the corresponding 2-pyrrolidone compound 19 wherein A is a double bond.

The reactions necessary to produce the products of the invention are arranged in order so that no epimerization of the optically active center at C5 will occur.

The first two steps of the reaction sequence are the condensation and esterification of D-glutamic acid to produce the corresponding D-methyl pyroglutamate of the structure:

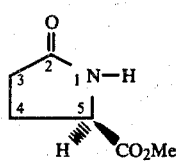

[E. Hardegger, et al., *Helv. Chem. Acta.*, 38, 312 (1955); E. Segel, *J. Am. Chem. Soc.*, 74, 851 (1952)].

The third, and known, step of the sequence shown in Scheme A as step (a) is the reduction of the 5-carboxymethyl group of the D-methylpyroglutamate to produce 5-D-hydroxymethyl-2-pyrrolidone. This reaction is most conveniently conducted by employing a variation of the method reported by V. Bruckner, et al. [*Acta. Chem. Hung. Tomus*, 21, 106 (1959)]. The D-methyl pyroglutamate is stirred with lithium borohydride in dry tetrahydrofuran or other ethereal solvent until the reduction is substantially complete. Isolation of the product in the reported manner gives 5-D-hydroxymethyl-2-pyrrolidone of the structure:

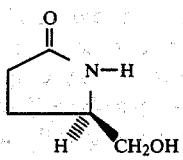

In order to alkylate the amide nitrogen of 5-D-hydroxymethyl-2-pyrrolidone, it is appropriate to protect the labile 5-hydroxymethyl hydrogen with the known tetrahydropyranyl group. This protection (Scheme A, step (b)) is most conveniently accomplished by contacting 5-D-hydroxymethyl-2-pyrrolidone with dihydropyran in the presence of an organic acid such as p-toluene sulfonic acid and in an inert solvent such as methylene chloride, chloroform, tetrahydrofuran or diethoxy ethane. The appropriate temperature range for this reaction is from that of an ice bath to that of refluxing solvent and preferably ambient. After the formation of 5-D-(tetrahydropyran-2'-yloxymethyl)-2-pyrrolidone 1 is substantially complete, usually overnight, it is isolated by first removing the organic acid by basic extraction and removing the solvent and any excess dihydropyran by vacuum evaporation techniques. The product is most commonly purified by column chromatography.

Other protecting agents that can be employed with equal facility include any which will protect the hydroxyl from alkylation. Some examples are benzyl, acetyl, dimethyl-t-butyl silyl and 1-ethoxyethyl. These protecting agents are readily available and can be attached to the 5-hydroxymethyl group by known methods. Their selection for synthetic purposes will depend upon the protecting group at C7'. For instance, if it is desired to employ N-tetrahydropyran-2-yl as a protecting group for the acidic hydrogen of a C7' tetrazol-5-yl (W), appropriate C3" hydroxyl protecting groups (T) would be acetyl or dimethyl-t-butyl silyl.

The 1-(alkylated)-2-pyrrolidone compounds (17 and 18 Scheme A) are prepared by a combination of two reactions which are performed upon 5-D-(tetrahydropyran-2'-yloxymethyl)-2-pyrrolidone 1 of any of its T group analogs. First, the sodium or lithium salt of pyrrolidone 1 is prepared by contacting a solution of compound 1 in an inert organic solvent such as tetrahydrofuran, diethoxyethane or dioxane with a base such as n-butyl lithium, phenyl lithium or especially sodium hydride. The appropriate temperature range for this salt formation is ambient to that of refluxing solvent and preferably ambient. All base must be reacted before starting the alkylation which usually requires times of 1 to 4 hours. Then, the desired 1-(alkylated)-2-pyrrolidone compounds 17 and 18 are respectively formed by contacting the above prepared lithium or sodium salt of 2-pyrrolidone compound 1 with an alkylating agent of the structure:

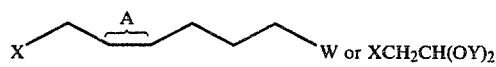

wherein X is Cl, I and especially Br,

W and A are each defined as above and

Y is alkyl having from one to three carbon atoms.

This second part of the alkylation procedure is usually conducted by addition of a mixture of the alkylating agent in the inert organic solvent previously defined or especially by addition of a mixture of the alkylating agent in a polar aprotic organic solvent such as dimethylformamide or dimethylacetamide to the above formed mixture of the sodium or lithium salt of pyrrolidone 1 in an inert organic solvent and then by allowing contact between the mixture of alkylating agent and 2-pyrrolidone sodium or lithium salt at temperatures of ambient to solvent reflux until the alkylation is substantially complete, usually overnight.

Of course, the alkylated 2-pyrrolidone resulting from use of XCH₂CH-(OY)₂ can also be prepared by employing XCH₂CO₂Et as the alkylating agent followed by selective conversion of the ester group of the resultant 1-(2'-ethyl acetate)-5-(substituted)-2-pyrrolidone to aldehyde.

When there is the possibility of having an acidic hydrogen present in W, the alkylation procedure is most conveniently executed by protecting or otherwise removing that acidic hydrogen. For example, in the case where R₃ is hydrogen, the best method is employment of an ester derivative which can then be removed by alkaline hydrolysis at the end of the synthetic sequence. In the case where W is tetrazol-5-yl, the best method is replacement of the acidic hydrogen by an acyloxymethyl as defined above, a phthalidyl group [W. v.Daehne, *J. Med. Chem.*, 13, 607 (1970); I. Isaka, et al., *Chem. Pharm. Bull.*, 24, 102 (1976)] or a tetrahydropyran-2-yl group. The first two groups for tetrazol-5-yl protection will also be removed by alkaline hydrolysis at the end of the synthesis (Scheme B) but the THP group will be removed by acidic hydrolysis. It will be assumed in the ensuing discussion that the acidic hydrogen of the W group has been protected unless otherwise stated.

The character of the C2'-C3' bond of the 2-pyrrolidone compound 17 obtained from the alkylation step is determined by the nature of A in the alkylating agent

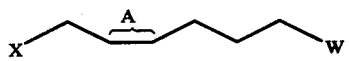

The selection of A will also determine the unsaturated or saturated character of the α-side chain of the final product of the synthesis; that is, whether the final product will be an 8-aza-11-desoxy PGE₁ or an 8-aza-desoxy PGE₂.

Obviously, the selection of A only causes a difference in the character of the C2'-C3' bond of the α-side chain and in fact, conversion from pyrrolidone compounds where A is a double bond to those where A is a single bond is possible at the pyrrolidone compound 17 stage of the synthesis. For instance, the 2-pyrrolidone compound 17 with the double bond at A may be converted to the 2-pyrrolidone compound 17 with the single bond at A by hydrogenation over a noble metal catalyst such as palladium on carbon at ambient temperature until 1 equivalent of hydrogen is absorbed.

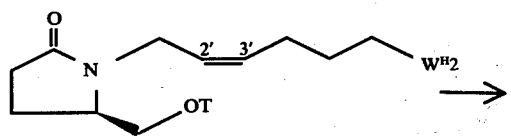

Compound 17 A = double bond

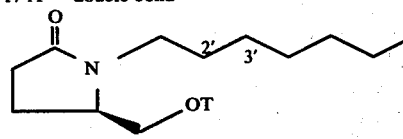

Compound 17 A = single bond

In either case, the protecting group T is removed (step d, Scheme A) by methods known to those familiar with the art in anticipation of the formation of the ω-side chain. The resulting 2-pyrrolidone compounds of the structure:

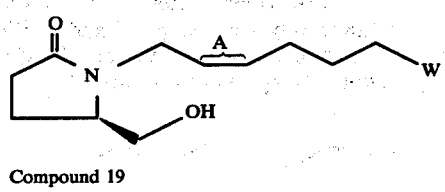

Compound 19 wherein W and A are each defined as above, are then carried through Schemes B, C and D to produce the novel final products of the present invention.

The above 2-pyrrolidone compound 19 can also be prepared by contacting the hydrolyzed form of the 2-pyrrolidone of the structure:

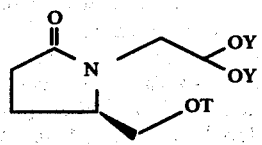

Compound 18 wherein Y and T are defined as above with a phosphorane of the structure:

Ph₃P=CH(CH₂)₃W

wherein W, defined as above, is unprotected, e.g. CO₂H or tetrazol-5-yl. The synthesis of the tetrazol-5-yl phosphorane will be found in U.S. Pat. No. 3,953,466.

This subset of reactions, illustrated by steps (f) and (g) of Scheme A, can be executed in the following manner. If the preferred T protecting group, tetrahydropyran-2-yl, is used in compound 18, then acid hydrolysis of compound 18 according to the usual method for acetal removal such as acetic acid in water at ca.40° C. will cleave both the tetrahydropyran-2-yl and the acetal to form 1-(ethan-2'-al)-5β-hydroxymethyl-2-pyrrolidone which can exist in intimate equilibrium with 4-aza-2-hydroxy-1-oxa-bicyclo[4,3,0]nonan-5-one 5.

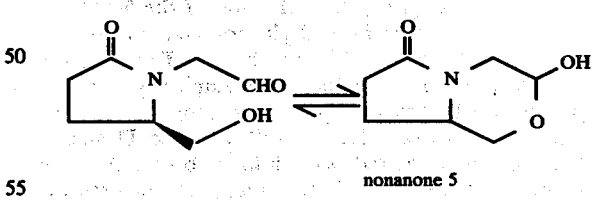

nonanone 5

The equilibrium mixture containing hemiacetal 5 can then be contacted with about 2 equivalents of phosphorane as defined above in polar aprotic solvent such as dimethylsulfoxide or a mixture of an ethereal and polar aprotic solvent such as tetrahydrofuran and dimethylsulfoxide at temperatures of 0° C. to 60°, usually overnight, to produce 2-pyrrolidone 19 wherein A is a double bond. It will be noted that the acidic hydrogen or group W can then be protected as an ester in the case of the carboxylic acid or as an N-acyloxymethyl, N-phthalidyl or N-tetrahydropyran-2-yl

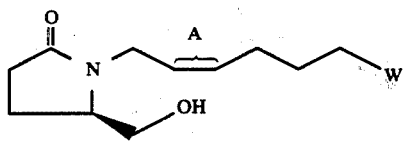

group in the case of tetrazol-5-yl. This 2-pyrrolidone 19 with A as a double bond can, if desired, be converted to 2-pyrrolidone 19 wherein A is a single bond by the hydrogenation method described above.

Several of the final products of the present invention, the 2-pyrrolidone compounds 22, carb. and tet., are prepared by oxidation of the 5β-hydroxymethyl group of 2-pyrrolidone 19 and Horner-Wittig reaction of the thus formed 5β-formyl-2-pyrrolidone compound 20 with the sodium or lithium salt of a phosphonate of the structure

wherein R₂ is defined as above, followed by reduction of the thus formed 5-(4″-substituted-but-1″-en-3″-onyl) moiety of 2-pyrrolidone 21.

Scheme B illustrates this outlined process, the method of which attaches the ω-chain.

SCHEME B
ω-CHAIN ATTACHMENT

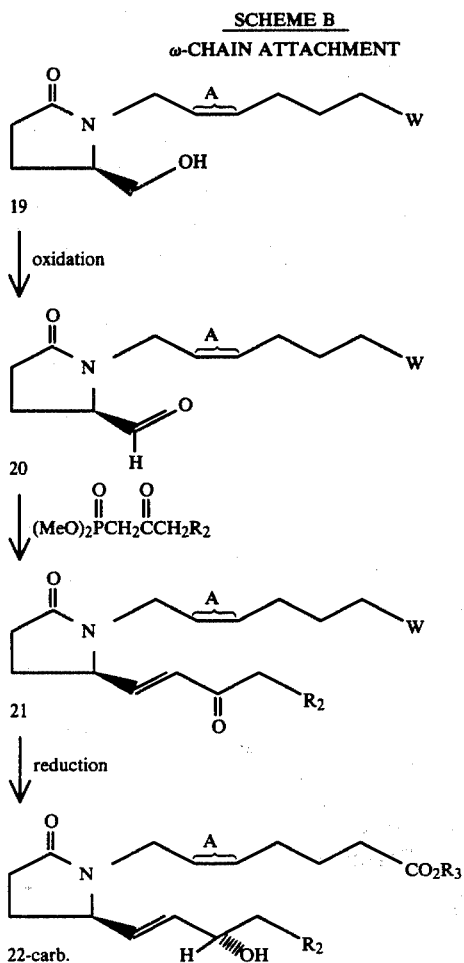

-continued
SCHEME B
ω-CHAIN ATTACHMENT

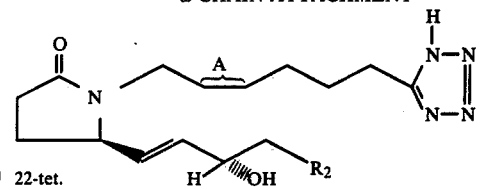

The aldehyde 20 is obtained from the 5β-hydroxymethyl-2-pyrrolidone compound 19 by a modification of the Pfitzner Moffatt oxidation [K. E. Pfitzner and M. E. Moffatt, J. Am. Chem. Soc., 87, 5661 (1965)] which avoids contact of the 5β-formyl compound 20 with water. For example, stirring a slurry of 1-(7′-methylheptanato)-5β-hydroxymethyl-2-pyrrolidone or other appropriate 5β-hydroxymethyl-2-pyrrolidone in an inert, hydrocarbon solvent such as toluene, xylene or especially benzene with dimethyl sulfoxide, a weak acid such as acetic acid or especially pyridinium trifluoroacetate and a water soluble diimide such as diethyl carbodiimide or especially dimethylaminopropylethylcarbodiimide or, if desired, its hydrochloride salt, at temperatures of 0° C. to ambient for 1 to 4 hours, will oxidize the primary alcohol 19 to aldehyde 20. Alternate methods to achieve oxidation include the usual Pfitzner-Moffatt reaction and oxidation with chromium trioxide-pyridine complex [R. Ratcliffe, et.al., J. Org. Chem., 35, 4000 (1970)] although the method of choice is the reaction described above.

The 5β-(4″-substituted but-1″-en-3″-onyl)-2-pyrrolidone compound 21 is prepared by contacting the 5β-formyl-2-pyrrolidone compound 20 with the sodium or lithium salt of a phosphonate of the structure:

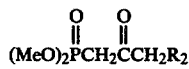

wherein R₂ is defined as above in a solution or slurry with an ethereal solvent such as tetrahydrofuran, dimethoxyethane or dioxane at temperatures from 0° to 50° C. until the reaction is essentially complete, as determined by reaction monitoring methods. The isolation of product from this Horner-Wittig reaction, the method of which is known to those familiar with the art, is accomplished in the usual fashion by chromatography. Other methods include high pressure liquid chromatography and in some cases fractional recrystallization. The method for the preparation of the phosphonates will be found in U.S. Pat. No. 3,932,389.

Reduction and, if desired, alkaline or acidic hydrolysis of the 2-pyrrolidone compound 21 produces several of the final products of the invention wherein Q is CO₂R₃ or tetrazol-5-yl. The reagent of choice for conducting the reduction is lithium triethylborohydride, but other selective reduction reagents which will reduce the ketone but no other groups, e.g. zinc borohydride or sodium borohydride, can be employed with equal facility. The usual solvents employed are ethereal in nature such as tetrahydrofuran and diethyl ether. The temperature selection will be based upon the activity of the reducing agent and in most cases it is convenient to employ a dry ice/acetone bath.

Under the usual reaction conditions, the reduction of the but-1″-en-3″-onyl moiety of the pyrrolidone 21 will actually product two 2-pyrrolidone compounds 22, which are diastereomers.

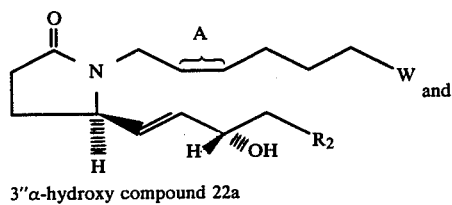

3″α-hydroxy compound 22a

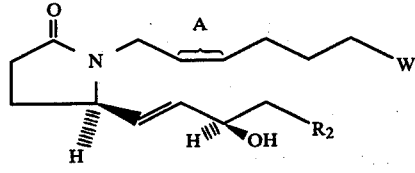

3″β-hydroxy compound 22b

Thus, these two compounds, which are separable by the common isolation techniques such as high pressure liquid chromatography, are both prepared by the described manner; and it is assumed that both are indicated even though the α isomer is shown throughout. If the separation of the two diastereomers is not done, then a mixture of the two compounds will result and is indicated as:

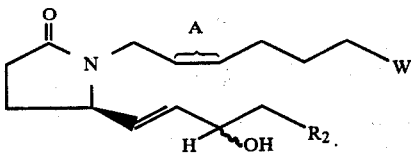

and is taken to mean a mixture of the α epimer and the β epimer.

After isolation of the product of the above reduction reaction in the usual manner, the protecting group on the acidic position of the C7 group W, can be removed, if desired, using conditions common for the removal of such groups. For instance, if an alkyl ester was selected as W and the acid is desired, simple alkaline hydrolysis with one equivalent of base at ambient temperature to that of refluxing solvent, usually overnight, will yield after neutralization the carboxylic acid. In a like manner, the phthalidyl and acyloxymethyl groups can be removed, but the tetrahydropyran-2-yl (THP) group will be removed with acid such as acetic acid in water or p-toluene sulfonic acid in methanol at ambient temperature to 50° usually overnight.

The products of the present invention wherein A and B are each single bonds, e.g. compound 23 carb. and tet., are prepared by catalytic reduction of the 3″-tetrahydropyran-2‴-yloxy derivative of 2-pyrrolidone 22 wherein A is a single bond. That sequence is outlined in Scheme C.

Alternatively, the pyrrolidone compounds 23 can be produced by catalytic reduction of the 3‴-tetrahydropyran-2‴-yloxy derivative of 2-pyrrolidone 22 wherein A is a double bond. In this case, A and B will be reduced to single bonds at the same time.

A = single bond

SCHEME C

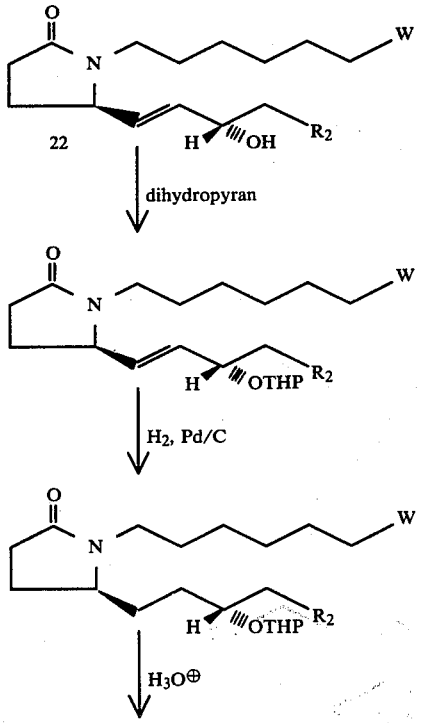

-continued
SCHEME C

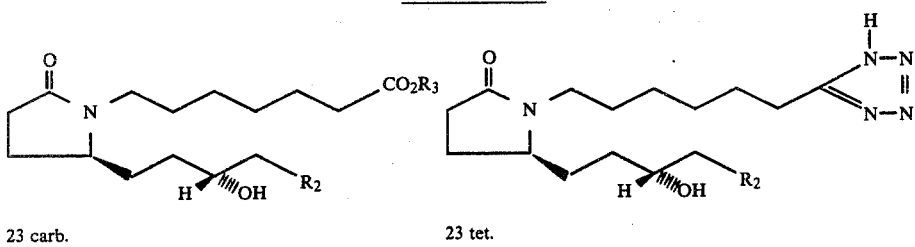

23 carb.          23 tet.

The tetrahydropyran-2′′′-yloxy derivative of compound 22 wherein A is a single bond is formed in the same manner as that described for 5-D-(tetrahydropyran-2-yloxymethyl)-2-pyrrolidone 1. Then, hydrogenation over noble metal catalysts such as palladium on carbon or platinum oxide in solvents such as ethyl acetate, methanol or ethanol at ambient to reflux temperatures until 1 equivalent of hydrogen is absorbed followed by removal of the tetrahydropyran-2″-yl group and, if desired, the W protecting group by the usual methods will allow the preparation of the 8-aza-11-desoxy prostaglandin $E_0$ compounds 23.

The products of the present invention wherein Q is

are prepared from the tetrahydropyran-2′′′-yloxy derivatives of compounds 22 and 23 having a $CO_2H$ group at W. That synthetic sequence is outlined in Scheme D wherein $R_5$ is defined as above. These acid derivatives, compounds 24 and 25, are formed according to well-known methods described for imide and sulfonimide preparations from carboxylic acids. The preferred method is that according to the procedure of Speziale and Hurd where the acyl or sulfonyl isocyanate is contacted with the above cited derivatives of compounds 22 and 23 in an inert solvent such as ether or tetrahydrofuran at temperatures of ambient to solvent reflux, usually overnight. See the following: [A. J. Speziale, et. al., *J. Org. Chem.*, 30, 4306 (1965), C. D. Hurd and A. G. Prapas, *J. Org. Chem.*, 24, 388 (1959); reactions of isocyanates with carboxylic acids in "Survey of Organic Synthesis", C. A. Beuhler, D. E. Pearson, Wiley Interscience, New York, 1970, N-acylation of amides and imides, J. March, "Advanced Organic Chemistry: Reactions, Mechanism and Structure", McGraw-Hill, New York, 1968, p. 340].

SCHEME D
IMIDE AND SULFONIMIDE DERIVATIVES

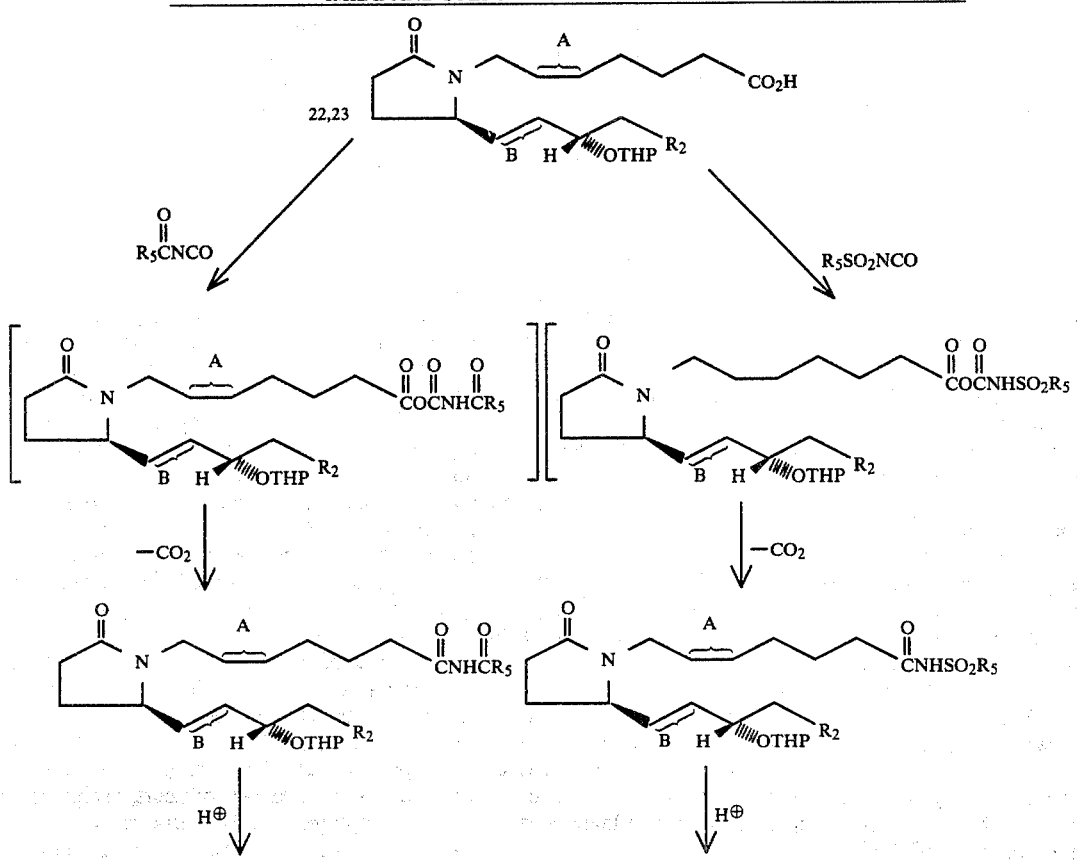

-continued
SCHEME D
IMIDE AND SULFONIMIDE DERIVATIVES

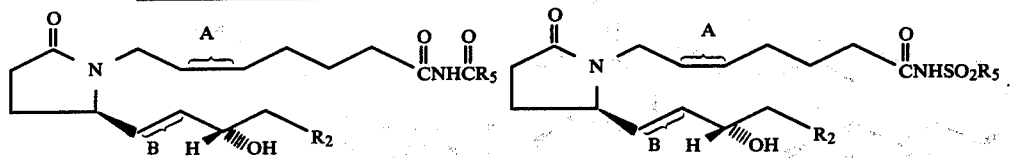

24          25

In numerous in vivo and in vitro tests it has been demonstrated that the new prostaglandin analogs possess physiological activities of greater selectivity, potency, and duration of action than those exhibited by the natural prostaglandins. These tests include, among others, a test for effect on isolated smooth muscle from guinea pig uterus, inhibition of histamine-induced bronchospasm in the guinea pig, effect on dog blood pressure, diarrheal effect in the mouse, and inhibition of stimulated gastric acid secretion in dogs.

The physiological responses observed in these tests are useful in determining the utility of the test substance for the treatment of various natural and pathological conditions. The possible utilities investigated include: vasodilator activity, antihypertensive activity, bronchodilator activity, antifertility activity and antisecretory activity.

The novel 8-aza-11-desoxy prostaglandins of the instant invention possess highly selective activity profiles compared with the corresponding naturally-occurring prostaglandins and, in many cases, exhibit a longer duration of action. For instance, the pyrrolidones of the present invention having the substitutions of aryl (including phenyl, substituted phenyl and α-thienyl) at $R_2$ and carboxylic acid, carboxylic ester or tetrazol-5-yl at Q possess useful vasodilator and antihypertensive activity. In addition they display antisecretory activity. A prime example of the therapeutic importance of these pyrrolidone compounds is 1-(6'-carboxyhexyl)-5β-(3"-hydroxy-4"-phenylbut-1"-enyl)-2-pyrrolidone which exhibits hypotensive activity of greater potency than $PGE_2$ itself when administered intravenously to anesthesized dogs. These compounds also exhibit good antisecretory activity when administered orally to pouch dogs that have been stimulated to secrete gastric acid. However, their other activities including bronchodilation and effect on uterine smooth muscle are greatly diminished compared to $PGE_2$.

Another example of the therapeutic importance of pyrrolidones of the instant invention is the selective antisecretory activity of compounds having the substitutions of aryloxy (including phenoxy and substituted phenoxy) at $R_2$ and carboxylic acid, carboxylic ester or imide, tetrazol-5-yl or sulfonimide at Q. For example, 1-(6'-carboxyhexyl-5β-(3"-hydroxy-4"-phenoxy-but-1"-enyl)-2-pyrrolidone displays good antisecretory activity when administered orally to pouch dogs but displays diminished hypotensive activity i.v. in anesthesized dogs and diminished uterine smooth muscle activity compared to $PGE_2$.

The new compounds of this invention can be used in a variety of pharmaceutical preparations which contain the compounds or a pharmaceutically acceptable salt thereof. They may be administered by a variety of routes which will depend upon the type of ailment and the condition of the individual.

The 8-aza-11-desoxy-16-aryl-ω-tetranorprostaglandin compounds of the present invention are useful vasodilator and antihypertensive agents. For treatment of injection at doses of about 0.5–10 microgram/kg. or preferably in the form of capsules or tablets at doses at 0.005 to 0.5 mg./kg./day.

The 8-aza-11-desoxy-16-aryloxy-ω-tetranorprostaglandin compounds of the present invention are useful antisecretory agents. For treatment of peptic ulcer, these drugs may be administered in the form of capsules or tablets at doses of 0.005 to 0.5 mg./kg./day. The 16-aryl prostaglandins of the present invention may also be used in this manner depending on the correlation with the antihypertensive activity they also possess.

Pharmacologically acceptable salts useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylamine, β-phenylethylamine, ethylenediamine, diethylenetriamine, and other aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methyl-pyrrolidine, 1,4-dimethylpiperazine, 2-methylpiperdine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)-aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

To prepare any of the numerous formulations possible, various reactioninert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims. The spectral data were obtained on a Varian T-60 or an A-60 NMR, a Perkin-Elmer Grating Infrared Spectrometer and an LKB-9000 mass spectrometer. The infrared data are given in reciprocal centimeters and the NMR data are given in δ parts per million using TMS as a standard.

In general, the temperatures of the reactions described in the examples, when unspecified, will be taken to mean ambient or room temperature which varied from 15° to 30° C.

The time requirement of the reactions described in the examples, unless otherwise stated, was determined by monitoring with thin layer chromatography (TLC). The usual TLC system was silica gel on glass (E. Merck Silica Gel plates, E. Merck Dormstadt, W. Germany) with benzene/ether or methanol/chloroform as eluants and vanillin/ethanol or iodine as developers. ["Introduction to Chromatography" J. M. Bobbitt, A. E. Schwarting, R. J. Gritter, Van Nostrand-Reinhold, N.Y. 1968]. As a general rule, the reaction in question was deemed essentially complete when the TLC spot representing the critical starting material had disappeared or had quit changing.

EXAMPLE 1

5β-(Tetrahydropyran-2'-yloxymethyl)-2-pyrrolidone 1

Into a flame dried flask under a nitrogen atmosphere was put 2.54 g. (22.1 mmoles) 5-D-hydroxymethylene-2-pyrrolidone, prepared according to the method of V. Bruckner et. al., *Acta Chim. Hung. Tomus*, 21, 106 (1959), and 50 ml. methylene chloride. To this solution at 0° C. to 5° C. was then added 3.72 g. (44.2 mmoles) redistilled dihydropyran and 0.2 g. p-toluenesulfonic (tosic)acid. The solution was then allowed to warm to room temperature and to stir overnight. After dilution of the reaction with 20 ml. ethyl acetate, the solution was extracted with 2×5 ml. saturated sodium bicarbonate solution and 1×10 ml. saturated brine. The organic layer was dried with magnesium sulfate, filtered to remove the drying agent, and the solvent was removed in vacuo to give 4.1 g. yellow oil. This oil was chromatographed on a 50 g. column of Merck silica gel packed in chloroform. Elution with 1 L. chloroform removed less polar impurities. Elution with 2% methanol in chloroform and collection of 10 ml. fractions separated and purified the product. Combination of product fractions and removal of solvent in vacuo gave 3.95 g. of the title compound 1 as a yellow oil, 90% yield. NMR T-60(DCCL$_3$)b.s. δ6.60 ppm (1H), m. δ4.60 ppm (1H), m. δ4.05-δ3.25 ppm (5H), m. δ2.50-δ2.10 ppm, m. δ2.00-δ1.40 ppm (1OH). IR(CHCl$_3$ solution) 3425, 2980, 2930, 2850, 1680, 1250-1200, 1025 cm$^{-1}$ Additionally, the dimethyl-t-butyl silyl protecting group can be employed in place of the tetrahydropyran-2-yl group by applying the procedure of E. J. Corey, et. al., *J. Am. Chem. Soc.*, 94, 6190 (1974) to 5-D-hydroxymethylene-2-pyrrolidone.

EXAMPLE 2

1-(7'-(Ethylheptanato)-5β-(tetrahydropyran-2''-yloxymethyl)-2-pyrrolidone 2

Into a flame dried flask containing a nitrogen atmosphere was put 0.725 g. (18.7 mmoles) of 62% sodium hydride dispersion in mineral oil and 10 ml. dry THF. To this mechanically stirred slurry was then slowly added dropwise 3.74 g. (18.7 mmoles) of 5-D-(tetrahydropyran-2-yloxymethyl)-2-pyrrolidone 1 in 10 ml. dry THF. After the addition was complete, the thick slurry was stirred for 30 minutes until all hydrogen evolution had ceased.

The alkylation of the sodium salt was then performed.

To this slurry at room temperature was then added dropwise 5.34 g. (22.5 mmoles) of ethyl-7-bromoheptanoate in 15 ml. dry DMF. At the completion of the addition, ca. 15 minutes, the slurry had dissolved and sodium bromide slowly started to precipitate from the solution. The reaction was stirred overnight, then filtered, and the solvent was removed in vacuo from the filtrate. To the residue was then added 100 ml. ethyl acetate and this organic solution was extracted with 2×20 ml. water. After drying the organic layer with magnesium sulfate and filtering it to remove the drying agent, the solvent was removed in vacuo from the filtrate to give a yellow oil which was chromatographed on a 120 g. column of Merck silica gel packed in chloroform. Elution with: (a) 250 ml. of chloroform; (b) 500 ml. 5% ethyl acetate in chloroform; (c) 1 L. 10% ethyl acetate in chloroform; and automatic collection of 10 ml. fractions allowed the separation and purification of the product. The product fractions were combined and stripped of solvent to yield the title compound 2 as a colorless oil 3.39 g. 51% yield.

NMR T-60 (DCCl$_3$): M δ4.60 ppm (1H), q. δ4.17 ppm J$_1$=8 hz., m, δ4.00-2.70 ppm (9H), m, δ2.6-1.4 ppm, t. δ1.3 ppm J$_1$=8 hz. (23H)

IR (HCCl$_3$) solution) 2975, 2915, 2840, 1720, 1665, 1450, 1250-1200, 1125, 1025 cm$^{-1}$.

MS-heated inlet (m/e-%) 356-1%, 355-3%, 310-17%, 240-100%, 194-83%.

The foregoing procedure can be adapted to the preparation of pyrrolidones of the structure below by substitution of the appropriate alkylating agent for ethyl-7-bromoheptanoate and optionally by employment of the dimethyl-t-butyl silyl analog of pyrrolidone 1.

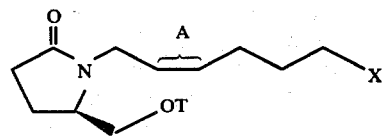

X=
—CO$_2$C$_6$H$_5$
—CO$_2$CH$_3$
N-(tetrahydropyran-2-yl)tetrazol-5-yl
N-(acetyloxymethyl)tetrazol-5-yl
A=single or cis double bond.
T=THP or dimethyl-t-butyl silyl As stated the 1-(substituted)-5β-(tetrahydropyran-2''-yloxymethyl or dimethyl-t-butyl siloxy methyl)-2-pyrrolidones can be prepared by substitution of the appropriate alkylating agent for the ethyl-7-bromoheptanoate. For instance, if 1-(6'-carboxymethylhex-2'-enyl)-5β-(tetrahydropyran-2''-yloxymethyl)-2-pyrrolidone is to be prepared, the alkylating agent will be methyl-7-bromohept-5-enoate. If 1-(6'-1'''-acetyloxymethyltetrazol-5'''-ylhexyl)-5β-(tetrahydropyran-2''-yloxymethyl)-2-pyrrolidone is to be prepared, the alkylating agent will be 6-bromo-1-(1'-acetyloxymethyltetrazol-5'-yl)-n-hexane.

1-(2,2-Diethoxyethyl)-5β-(tetrahydropyran-2''-yloxymethyl)-2-pyrrolidone 3 can also be prepared by the same procedure by employing 2-bromo-acetaldehyde diethyl acetal as the alkylating agent.

The preparation of 6-bromo-1-tetrazol-5'-yl-n-hexane can be accomplished by the following method.

A mixture of 2.98 g. (23.5 mmoles) 7-hydroxyheptanenitrile, 1.60 g. (30.0 mmoles) ammonium chloride, 0.032 g. (0.76 mmole) lithium chloride, 1.91 g. (29.3 mmoles) sodium azide and 50 ml. dimethyl formamide can be heated to 120° under nitrogen with stirring for 18 hours or until the reaction is essentially complete. The dimethyl formamide can then be removed in vacuo and the resulting residue can be purified by one of several methods such as chromatography or extraction. This product, 6-hydroxy-1-(tetrazol-5-yl)hexane, can then be treated with phosphorus tribromide under appropriate conditions to produce 6-bromo-1-(tetrazol-5-yl)hexane. The N'-acetyloxymethyl group can be attached by employing the method of W. V. Daehne et. al. opt. cit. while the N-tetrahydropyran-2-yl group can be attached according to the method of Example 1.

Treatment of 7-(tetrahydropyran-2'-yloxy)hept-5-ynenitrile in the same manner as above will allow preparation of 6-(tetrahydropyran-2'-yloxy)-1-(tetrazol-5'-yl)hex-4-yne. This material can then be converted into 6-bromo-1-(tetrazol-5'-yl)hex-4-ene according to the procedure of Ger. Offen. 2,121,361 (C.A. 76:24712d). Of course, the starting hept-5-ynenitrile can also be hydrogenated to the olefin before converting the nitrile to the tetrazole, essentially by following the same procedure. Again the protecting groups for the acidic hydrogen of the tetrazol-5-yl can be attached by the above methods.

EXAMPLE 3

1-(7'-Methylheptanato)-5β-hydroxymethyl-2-pyrrolidone 4

To a solution of 200 ml. methanol and 3.99 g. THP-pyrrolidone 2 was added 79 mg p-toluene sulfonic (tosic) acid and the solution was refluxed overnight. After work up as described below, an NMR spectrum of the reaction mixture revealed the presence of a small amount of starting ethyl ester. Therefore, the reaction mixture was redissolved in 160 ml. methanol, 0.080 g. tosic acid added, and the reaction again refluxed overnight. Removal of the solvent in vacuo from the reaction gave a yellow oil which was dissolved in ethyl acetate and extracted with 1×10 ml. of a 1:2 mixture of saturated sodium bicarbonate and half saturated Rochelle's salt solution. The organic phase was dried over magnesium sulfate, filtered and the solvent evaporated to give the title compound 4 as a clear yellow oil. 2.528 g (88%).

NMR A-60 (DCCl₃) s. δ3.86 ppm, m. δ4.00–3.33 ppm, m. δ3.20–δ2.70 ppm (13H), m. δ2.50–δ2.00 ppm, m. δ1.90–δ1.20 ppm (10H), partial spectrum.

IR (HCCl₃ solution) 3550–3100, 2980, 2910, 2840, 1720, 1650, 1450, 1425, 1410, 1250–1190 cm⁻¹.

MS, LKB 9000, solid inlet (m/e-%)70 eV 226–26%, 194–19.8% 74–100% 13 eV 257–3.3%, 226–100% 168–24.6%.

Alternatively the tetrahydropyran-2'''-yl group can be removed by hydrolysis in a 65:35 mixture of glacial acetic acid:water for ca. 18 hours essentially according to the procedure of Example 14.

In this case, the ethyl ester group of pyrrolidone 2 will be kept intact.

The foregoing acetic acid, water hydrolysis procedure can also be used to remove the tetrahydropyranyl protecting group from the other pyrrolidone products of Example 2 which then will produce the corresponding 1-(substituted)-5β-hydroxymethyl-2-pyrrolidones. However, if the tetrazol-5-yl protecting group is tetrahydropyran-2-yl, then it will be appropriate to employ the dimethyl-t-butyl silyl group as T. This silyl group can be selectively removed with tetra n-butyl ammonium fluoride according to the method of Corey, opt. cit.

On application of the acetic acid procedure to 1-(2,2-diethoxyethyl)-5-(tetrahydropyran-2''-yloxymethyl)-2-pyrrolidone 3 of Example 2, removal of the tetrahydropyranyl group will be accompanied by cleavage of the acetal and cyclization, to yield as product an equilibrium mixture of the open form and 4-aza-2-hydroxy-1-oxa-bicyclo[3,4,0]nonan-5-one 5.

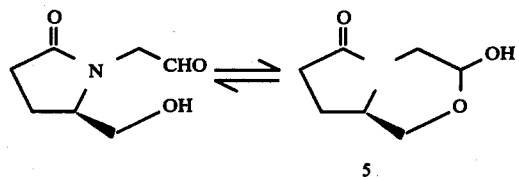

5

The equilibrium mixture containing compound 5 can be converted to 1-(substituted)-5β-hydroxymethyl-2-pyrrolidones by the following procedure.

To a solution of 23.04 g. (52.0 mmoles) of 5-triphenylphosphoniopentanoic acid (bromide salt) in 46 ml. dry dimethyl sulfoxide can be added dropwise 49.3 ml. (98.6 mmoles) of a 2.0 N solution of sodium methylsulfinylmethide in dimethyl sulfoxide. To the resultant red solution can then be added over the course of 1.0 hour 3.27 g. (20.8 mmoles) of 4-aza-2-hydroxy-1-oxa-bicyclo[3,4,0]nonan-5-one 5 in dry dimethyl sulfoxide (63 ml.). After being stirred for an additional half hour or until substantially complete, the reaction can be poured into 600 ml. of ice-water and then can be extracted with 2×300 ml. of ethyl acetate. The cold aqueous layer can be covered with ethyl acetate and acidified to pH~3 with 10% hydrochloric acid after which the aqueous layer can be extracted with 2×200 ml. of ethyl acetate. The combined organic extracts are washed with water, followed by brine, and the organic layer can be dried over anhydrous sodium sulfate. Concentrating the filtered organic layer will afford crude 1-(6'-carboxyhex-2'-enyl)-5β-hydroxymethyl-2-pyrrolidone which can be chromatographed. The acid can then be esterified with diazomethane.

This procedure can also be used to prepare 1-(substituted)-5β-hydroxymethyl-2-pyrrolidones of the structure,

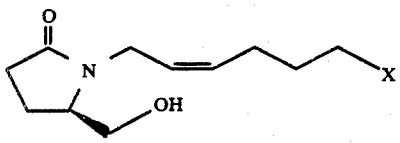

wherein X is the same as that of Example 2, by substituting the appropriate phosphonium salt for 5-triphenylphosphonopentanoic acid and then protecting the acidic hydrogen with an N-acyloxymethyl group according to the procedure described by W. V. Daehne et. al., op. cit., with an N-tetrahydropyran-2-yl group according to the procedure of Example 1 or by esterifying in the case of the carboxy acid.

EXAMPLE 4

1-(7'-Methylheptanato)-5β-formyl-2-pyrrolidone 6

To a flame dried flask containing a nitrogen atmosphere was added 0.1286 g. (0.5 mmoles) 1-(7'-methylheptanato)-5β-hydroxymethyl-2-pyrrolidone 4 in 5 ml. dry benzene. To this solution 0.1286 g. (1.5 mmoles) dimethylaminopropylethylcarbodiimide hydrochloride (DAPC) and 0.142 ml. (2 mmoles) dimethylsulfoxide were added followed after five minutes by 0.108 g. (0.55 mmoles) of pyridinium trifluoroacetate. The reaction was stirred under a nitrogen atmosphere at room temperature for 1.75 hours, then the benzene was decanted and the viscous second phase which had formed at the bottom of the flask was washed with 3×5 ml. benzene. The benzene solutions were combined and the solvent was removed in vacuo to give 0.152 g. of the title compound 6 as a clear yellow oil. The crude product was used immediately and without further purification in the next reaction.

NMR T-60 (DCCl$_3$), d. δ9.72 ppm J$_1$=3 hz(1H), m. δ4.37–δ4.07 ppm (1H), s. δ3.70 ppm (3H). partial spectrum The foregoing procedure can also be used to oxidize the other 1-(substituted)-5β-hydroxymethyl-2-pyrrolidones of Example 3 to the corresponding 1-(substituted)-5β-formyl-2-pyrrolidones.

EXAMPLE 5

1-(7'-Methylheptanato)-5β-(4"-phenylbut-1"-en-3"-onyl)-2-pyrrolidones 7

Into a flame dried flask containing a nitrogen atmosphere was put 0.1188 g. (2.97 mmoles) of a 60% sodium hydride mineral oil dispersion and 5 ml. THF. To this slurry was added a solution of 0.7815 g. (3.24 mmoles) of dimethyl(3-phenylpropan-2-onyl)phosphonate in 5 ml. THF. After the evolution of hydrogen ceased, a white suspension occurred which was stirred for fifteen minutes. To this suspension was added 0.6894 g. (2.70 mmoles) of 1-(7'-methylheptanato)-5β-formyl-2-pyrrolidone 6 in 10 ml. THF over a period of 1 minute. Within five minutes, the reaction became a clear yellow solution and was stirred for an additional two hours. The reaction was quenched with glacial acetic acid to pH 5. The solvent was removed in vacuo and the residue was taken up in 100 ml. ethyl acetate. The organic solution was extracted with 2×10 ml. saturated aqueous sodium bicarbonate, 3×10 ml. water and 1×10 ml. saturated brine. The organic layer was dried over magnesium sulfate, filtered and the solvent removed in vacuo to give 1.141 g. yellow oil. This crude product was chromatographed on a 35 g. column of E. Merck silica gel packed in ethyl acetate. Elution with ethyl acetate and automatic collection of 10 ml. fractions allowed the purification of the product. The product fractions were combined and the solvent removed in vacuo to give 0.614 g. of the title compound 7 as a colorless oil (61% yield from the starting alcohol).

NMR T-60(DCCl$_3$)s. δ7.33 ppm (5H), dofd. δ6.73 ppm J$_1$=7 hz J$_2$=16 hz, d. δ6.60 ppm J$_2$=16 hz (2H), m. δ4.27 ppm center (1H), s. δ3.93 (2H), s. δ3.73 ppm (3H). partial spectrum.

IR(CHCl$_3$ solution) 2980, 2900, 2840, 1725, 1685(sh), 1675, 1625, 1250–1200 cm$^{-1}$ MS,LKB9000 (m/e %)70 eV 372–20%, 371–82%, 252–96%, 226–24%, 194–35%, 12 eV 372–18%, 371–100%, 252–24%, 226–39%.

The other 1-(substituted)-5β-formyl-2-pyrrolidone compounds of Example 4 can be employed in the foregoing procedure in place of pyrrolidone 6 to make the corresponding 1-(substituted)-5β-(4"-phenylbut-1"en-3"-onyl)-2-pyrrolidone compounds. In addition, phosphonates of the structure:

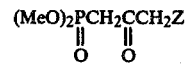

Z=
—C$_6$H$_4$CH$_3$ (m)
—α-thienyl
—C$_6$H$_4$OCH$_3$ (p)
—C$_6$H$_4$—C$_6$H$_5$ (m)
—C$_6$H$_4$CF$_3$ (p)
—C$_6$H$_4$Cl (o)

can be substituted for dimethyl(3-phenylpropan-2-onyl)phosphonate to make the corresponding 1-(substituted)-5β-(4"-substituted but-1"-en-3"-onyl)-2-pyrrolidone compounds. Hereafter, all pyrrolidones including the 4"-phenyl compounds shall be known as 1-(substituted)-5β-(4"-substituted but-1"-en-3"-onyl)-2-pyrrolidones.

EXAMPLE 6

1-(7'-Methylheptanato)-5β-(3"-hydroxy-4"-phenylbut-141-enyl)-2-pyrrolidone 8

To a flame dried flask equipped with a magnetic stirring bar, thermometer and containing a nitrogen atmosphere was added 0.5784 g. (1.56 mmoles) 1-(7'-methylheptanato)-5β-(4"-phenylbut-1"-en-3"-onyl)-2-pyrrolidone 7 in 20 ml. dry THF. The clear, colorless solution was cooled to −78° C. and 1.56 ml. (1.56 mmoles) lithium triethyl borohydride was added dropwise via syringe, needle and serum cap over a 15 minute period. After 1 hour, a TLC showed the absence of starting enone so the reaction was quenched with glacial acetic acid to pH 5 which was followed by removal of the solvent in vacuo. The residue was dissolved in 50 ml. ethyl acetate and this organic solution was then extracted with 1×10 ml. half saturated aqueous sodium bicarbonate, 4×10 ml. water and 1×10 ml. saturated brine. The organic layer was dried over magnesium sulfate, filtered and the solvent was removed in vacuo to give 700 mg. crude product. This product was chromatographed on a 9 g. silica gel column packed in ethyl acetate. Elution with ethyl acetate. Elution with ethyl acetate and automatic collection of 5 ml. fractions separated the product from impurities. Combination of product fractions and removal of solvent in vacuo gave 0.298 g. of the title compound 8 as a colorless oil (51% yield).

NMR T-60 (DCCl₃)s. δ7.37 ppm (5H), d. δ5.72 ppm J₁=7 hz, d. δ5.62 J₁=7 hz (2H), m. δ4.67–δ4.33 ppm, m. δ4.30–δ3.83 ppm (2H), s. δ3.73 ppm (3H), d. δ2.90 ppm J₂=6 hz (2H). partial spectrum.

IR (HCCl₃ solution) 3450–3200, 2975, 2900, 2830, 1725, 1665, 1250–1200 cm⁻¹.

The other 1-(substituted)-5β-(4''-substituted but-1''-en-3-oyl)-2-pyrrolidone compounds of Example 5 can be used in the foregoing procedure to prepare the corresponding 1-(substituted)-5β-(4''-substituted-3''-hydroxybut-1''-enyl)pyrrolidone compounds.

EXAMPLE 7

1-(6'-Carboxyhexyl)-5β-(3''-hydroxy-4''-phenylbut-1''-enyl)-2-pyrrolidone 9

To a solution of 69 mg. (0.185 mmoles) 1-(7:methylheptanato)-5β-(3-hydroxy-4-phenylbut-1-enyl)-2-pyrrolidone 8 in 3 ml. methanol was added 0.185 ml. (0.185 meq) 1N sodium hydroxide. The reaction solution was then refluxed overnight and then neutralized to pH 4 by addition of glacial acetic acid. The solvent was removed in vacuo and the oily residue was dissolved in 15 ml. ethyl acetate. The organic solution was extracted with 2×2 ml. water and 1×2 ml. saturated brine, dried with magnesium sulfate and filtered. The solvent was removed in vacuo to give the title compound 9 as a yellow oil; 59.4 mg., 89% yield.

NMR,T-60, DCCl₃, s. δ7.33 ppm (5H), b.s. δ6.30 ppm center (1H), d. δ5.73 ppm J₁=7 hz, d. δ5.6 ppm J₁=7 hz (2H), m. δ4.6–δ3.2 ppm (4H), d. δ2.93 ppm J₂=7 hz (2H). (partial spectrum).

IR, HCCl₃ solution, 3500–3100, 2980, 2920, 1700, 1600, 1250–1200 cm⁻¹.

Employment of the other 1-(substituted)-5β-hydroxybutenyl-2-pyrrolidones of Example 6 in place of pyrrolidone 8 in the foregoing procedure will allow cleavage of the methyl ester or the acyloxymethyl protecting groups and will allow the preparation of the following 8-aza-11-deshydroxy prostaglandin E₁ and E₂ compounds. The N-tetrahydropyran-2yl protecting group if one was employed, can be removed by the method of Example 3 or 14.

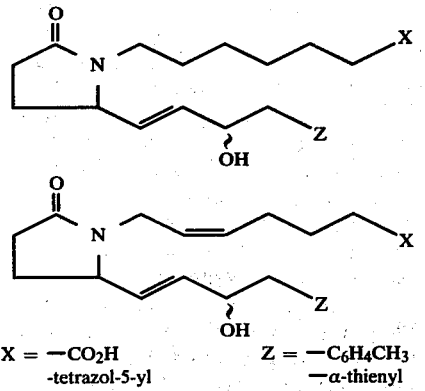

X = —CO₂H
    -tetrazol-5-yl

Z = —C₆H₄CH₃
    —α-thienyl
    —C₆H₄OCH₃
    —C₆H₄—C₆H₅
    —C₆H₄CF₃
    —C₆H₅

EXAMPLE 8

1-(7'-Methylheptanato)-5β-(4''-phenoxybut-1''-en-3''-onyl)-2-pyrrolidone 10

Into a flame dried flask containing a nitrogen atmosphere was put 22 mg. (0.55 mmoles) of a sodium hydride dispersion in mineral oil and 5 ml. THF. To this slurry was added a solution of 0.1549 g. (0.6 mmoles) dimethyl-(3-phenoxypropan-2-onyl)phosphonate in 5 ml. THF. After the evolution of hydrogen ceased, there was a clear, pale yellow solution which was stirred for fifteen minutes. To this solution was added 0.1277 g. (0.5 mmoles) 1-(7'-methylheptanato)-5β-formyl-2-pyrrolidone 6 in 5 ml. THF over a period of 1 minute. Within five minutes, the reaction had become a clear yellow solution and was stirred for an additional two hours. The reaction was quenched with glacial acetic acid to pH 5. The solvent was removed in vacuo and the residue was taken up in 50 ml. ethyl acetate. The organic solution was extracted with 2×5 ml. saturated aqueous sodium bicarbonate, 2×5 ml. water and 1×5 ml. saturated brine. The organic layer was dried over magnesium sulfate, filtered and the solvent removed in vacuo to give 0.231 g. yellow oil. This crude product was chromatographed on a 25 g. column of E. Merck silica gel packed in cyclohexane. Elution with 50% chloroform in cyclohexane and automatic collection of 10 ml. fractions allowed the purification of the product. The product fractions were combined and the solvent removed in vacuo to give 53.6 mg. of the title compound 10 (28% from the starting alcohol).

NMR T-60 (DCCl₃), m. δ7.40–6.70 ppm (5H), m. δ6.7–6.33 ppm (2H) s. δ4.67 ppm (2H), m. δ4.40–3.97 ppm (1H), s. δ3.67 ppm (3H). partial spectrum.

The other 1-(substituted)-6β-formyl-2-pyrrolidone compounds of Example 4 can be used in the foregoing procedure in place of pyrrolidone 6 to make the corresponding 1-(substituted)-5β-(4''-phenoxybut-1''-en-3''-onyl)-2-pyrrolidone compounds. In addition, phosphonates of the structure:

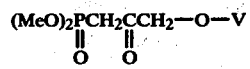

V =
   —C₆H₄CH₃ (p)
   —C₆H₄CF₃ (m)
   —C₆H₄—C₆H₄ (p)
   —C₆H₄OCH₃ (p)
   —C₆H₄—Cl (o)
   —C₆H₅ can be substituted for dimethyl(3-phenoxypropan-2-onyl)phosphonate to make those corresponding 2-pyrrolidone compounds.

EXAMPLE 9

1-7'-Methylheptanato)-5β-(3''-hydroxy-4''-phenoxybut-1-enyl)-2-pyrrolidone 11

To a flame dried flask equipped with a magnetic stirring bar, thermometer and containing a nitrogen atmosphere was added 0.1046 g. (0.27 mmoles) 1-(7'-methylheptanato)-5-(4''-phenoxybut-1''-en-3''-onyl)-2-pyrrolidone 10 in 5 ml. dry THF. The clear, colorless solution was cooled to −78° C. and 0.27 ml. (0.27 mmoles) lithium triethyl borohydride was added dropwise via syringe, needle and serum cap over a 15 minute period. After 1 hour, a TLC showed the absence of starting enone so the reaction was quenched with glacial acetic acid to pH 5 which was followed by removal of solvent in vacuo. The residue was dissolved in 25 ml. ethyl acetate and this organic solution was then extracted with 1×5 ml. half saturated aqueous sodium bicarbonate, 1×10 ml. water and 1×10 ml. saturated brine. The organic layer was dried over magnesium sulfate, filtered and the solvent was removed in vacuo to give 101 mg. crude product. This product was chromatographed on a 25 g. silica gel column packed in benzene. Elution with ethyl acetate and automatic collection of 5 ml. fractions separated the product from impurities but did not separate the two epimers. Combination of product fractions and removal of solvent in vacuo gave 85.6 mg. of the title compound 11 (82% yield).

NMR T-60 (DCCl$_3$) m. δ7.54–6.82 ppm (5H), m. δ5.94–5.73 ppm (2H), m. δ4.79–4.43 ppm (1H), m. δ4.33–3.94 ppm (3H), s. δ3.70 ppm (3H). partial spectrum.

IR (CHCl$_3$ solution) 3600–3100, 2980, 2920, 1730, 1670, 1600, 1200–1250 cm$^{-1}$ The other 1-(substituted)-5β-(phenoxybutenoyl)-2-pyrrolidone compounds of Example 8 can be substituted for pyrrolidone 10 in the foregoing procedure and will produce the corresponding 1-(substituted)-5β-(4''-phenoxy-3''-hydroxybut-1''-enyl)-2-pyrrolidone compounds.

EXAMPLE 10

1-(6'-Carboxyhexyl)-5β-(3''-hydroxy-4'-phenoxybut-1''-enyl)-2-pyrrolidone 12

To a solution of 50 mg. (0.128 mmoles) 1-(7'-methylheptanato)-5β-(3''-hydroxy-4''-phenoxybut-1''-enyl)-2-pyrrolidone 11 in 3 ml. methanol was added 0.128 ml. (0.128 mmoles) of 1 N sodium hydroxide. The reaction solution was refluxed overnight and then neutralized to pH 4 by addition of glacial acetic acid. The solvent was removed in vacuo and the oily residue was dissolved in 15 ml. ethyl acetate. The organic solution was extracted with 2×2 ml. water and 1×2 ml. saturated brine, dried with magnesium sulfate and filtered. The solvent was removed in vacuo to give the title compound 12 as a yellow oil; 48.0 mg. (99% yield).

NMR T-60 (DCCl$_3$) m. δ7.40–6.82 ppm (5H), m. δ6.73–6.17 ppm (2H), m. δ5.87–5.70 ppm (2H), m. δ4.7–4.4 ppm (1H), m. δ4.23–3.88 ppm (3H). partial spectrum.

IR (HCCl$_3$ solution) 3600–2900, 2920, 1700, 1670, 1600, 1200, 1250 cm$^{-1}$.

Employment of the other 1-(substituted)-5β-(hydroxyphenoxybutenyl)-2-pyrrolidone compounds of Example 9 in place of pyrrolidone 11 in the foregoing procedure will allow cleavage of the methyl ester or the acyloxymethyl groups and allow the preparation of the following 8-aza-11-deshydroxy prostaglandin E$_1$ and E$_2$ compounds. The N-THP protecting group can be cleaved according to the procedure of Example 14.

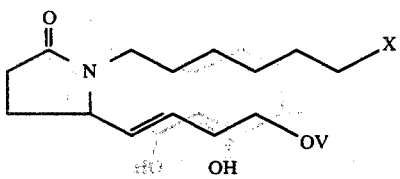

X = —CO$_2$H
   -tetrazol-5-yl

V = —C$_6$H$_4$CH$_3$ (p)
   —C$_6$H$_4$CF$_3$ (m)
   —C$_6$H$_4$—C$_6$H$_4$ (p)
   —C$_6$H$_4$OCH$_3$ (p)
   —C$_6$H$_4$—Cl (o)
   —C$_6$H$_5$

EXAMPLE 11

1-(7'-Methylheptanato)-5β-(3''-tetrahydropyran-2'''-yloxy-4''-phenylbut-1''-enyl)-2-pyrrolidone 13

Into a flame dried flask under a nitrogen atmosphere was put 128 mg. (0.342 mmoles) of 1-(7'-methylheptanato)-5β-(3''-hydroxy-4''phenylbut-1''-enyl)-2-pyrrolidone 9 and 5 ml. methylene chloride. To this solution at 0° C. to 5° C. was then added 0.062 ml. (0.684 mmoles) redistilled dihydropyran and 3 mg. tosic acid. The solution was then allowed to warm to room temperature and to stir overnight. The reaction was worked up by dilution with 10 ml. ethyl acetate, extraction with 2×2 ml. saturated sodium bicarbonate solution and 1×5 ml. saturated brine. The organic layer was dried with magnesium sulfate, filtered and the solvent was removed in vacuo to give 0.135 g. yellow oil. This was chromatographed on a 15 g. column of Merck silica gel packed in chloroform. Elution with 1 l. chloroform removed less polar impurities. Elution with 2% methanol in chloroform and automatic collection of 10 ml. fractions separated and purified the product. Combination of product fractions and removal of solvent in vacuo gave 0.1756 g. of the title compound 13 as a yellow oil.

NMR T-60 (DCCl$_3$) s. δ6.34 ppm (5H), m. δ5.77–5.37 ppm (2H), m. δ5.13–4.80 ppm (1H), s. δ3.7 ppm (3H). partial spectrum.

In addition, the 1-(substituted)-5β-(4''-substituted-3''-hydroxybut-1''-enyl)-2-pyrrolidones of Example 6, 7, 9 and 10 can be employed in this procedure to prepare the corresponding THP derivatives.

EXAMPLE 12

1-(7'-Methylheptanato)-5β-(3''-tetrahydropyran-2'''-yloxy-4''-phenylbutanyl)-2-pyrrolidone 14

To a solution of 156.5 mg. (0.342 mmoles) of 1-(7'-methylheptanato)-5β-(3''-tetrahydropyran-2'''-yloxy-4''-phenylbut-1''-enyl)-2-pyrrolidone 13 in 10 ml. ethyl acetate was added 31 mg. of 10% palladium on charcoal and the entire mixture placed on a Parr hydrogen reduction apparatus and shaken under a pressure of 50 lb. hydrogen for 4 hours. The slurry was then filtered through celite to remove the catalyst and the solvent was removed from the filtrate to give 158.2 mg. of the title compound 14.

NMR T-60 (DCCl$_3$) s. δ7.33 ppm (5H), m. δ5.13–4.67 ppm (1H), m. δ4.57–4.33 ppm (1H), s. δ3.73 ppm (3H). partial spectrum.

In addition, the other THP derivatives of Example 11 wherein A is a single bond can be employed in this procedure to prepare the corresponding hydrogenated derivatives.

EXAMPLE 13

1-(6'-Carboxyhexyl)-5β-(3''-tetrahydropyran-2'''-yloxy-phenylbutanyl)-2-pyrrolidone 15

To a solution of 1582 mg. (0.342 mmoles) of 1-(7'-methylheptanato)-5β-(3''-tetrahydropyran-2'''-yloxy-4''-phenylbutanyl)-2-pyrrolidone 14 in 5 ml. methanol was added 0.342 ml. (0.342 mmoles) of 1 N sodium hydroxide. The reaction solution was refluxed overnight and then neutralized to pH 4 by addition of glacial acetic acid. The solvent was removed in vacuo and the oily residue was dissolved in 15 ml. ethyl acetate. The organic solution was extracted with 2×2 ml. water and 1×2 ml. saturated brine, dried with magnesium sulfate and filtered. The solvent was removed in vacuo to give the title compound 15 as a yellow oil; 134.2 mg. (89% yield).

NMR T-60 (DCCl₃) s. δ7.37 ppm (5H), m. δ4.4–3.2 ppm, m. δ2.92 (2H). partial spectrum.

In addition, the other hydrogenated derivatives of Example 12 can be employed in this procedure to prepare the corresponding 6'-carboxylic acid and 6'-tetrazol-5-yl compounds.

EXAMPLE 14

1-(6'-Carboxyhexyl)-5β-(3''-hydroxy-4-phenylbutanyl)-2-pyrrolidone 16
(8-aza-11-deshydroxy-16-phenyl-16-ω-tetranor PGE₀ 16)

A solution of 134.2 mg. (0.3 mmoles) of compound 15 was stirred in 5 ml. of a 65:35 mixture of acetic acid:water overnight under nitrogen at ambient temperature. The solvent was then removed by vacuum evaporation using an oil vacuum pump and the residue azeotroped with benzene. The crude product was then chromatographed on 15 g. of ARCC7 silica gel by eluting with 2% methanol in chloroform to give 82 mg. of the title compound 16.

NMR T-60 (DCCl₃) s. δ7.17 ppm (5H), m. δ3.2–4.0 ppm (3H), d. δ2.77 ppm $J_H=7$ hz (2H). partial spectrum.

IR (HCCl₃ solution) 3600–3100, 2930, 2860, 1700, 1660, 1250, 1200, 710 cm⁻¹.

In addition, this procedure can be employed to remove the THP protecting group from the 6'-carboxylic acid and 6'-tetrazol-5-yl derivatives of Example 13 and the hydrogenated derivatives of Example 12.

EXAMPLE 15

1-(6'-N-Phenylimidohexyl)-5β-(3''-hydroxy-4''-phenyl-but-1''-enyl)-2-pyrrolidone To a solution of 64 mg. (0.171 mmoles) 1-(6'-carboxyhexyl)-5β-(4''-phenyl-3''-tetrahydropyran-2'''-yloxybut-1''-enyl)-2-pyrrolidone prepared according to the procedure of Example 11 in 10 ml. of dry tetrahydrofuran can be added 25.16 mg. (0.171 mmoles) of benzoyl isocyanate prepared according to the procedure of A. J. Speziale, *J. Org. Chem.*, 27, 3742 (1962) in 5 ml. of dry THF. After refluxing overnight, the solvent can be removed in vacuo and the reaction material deprotected (THP group removed) according to the procedure of Example 14 to give the title compound.

In a similar fashion, the following imide derivatives can be made: by substituting the other appropriately protected carboxylic acids of Examples 7, 10 and 14.

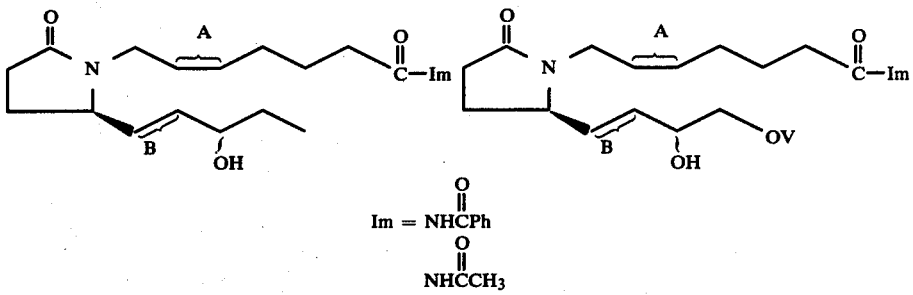

Z is defined in Example 7
V is defined in Example 10
A is a single or cis double bond
B is a single or trans double bond

EXAMPLE 16

1-(6'-N-Methylsulfonimidohexyl)-5β-(3''-hydroxy-4''-phenylbut-1''-enyl)-2-pyrrolidone To a solution of 64 mg. (0.171 mmoles) 1-(6'-carboxyhexyl)-5β-(4''-phenyl-3''-tetrahydropyran-2'''-yloxybut-1''-enyl)-2-pyrrolidone prepared according to the procedure of Example 11 in 10 ml. dry benzene can be added 20.7 mg. (0.171 mmoles) of methyl sulfonyl isocyanate (A. J. Speziale see Example 16) in 5 ml. dry benzene at ambient temperature. After refluxing overnight, the solvent can then be removed in vacuo and the resulting residue deprotected (THP group removed) according to the procedure of Example 14 to give the title compound.

By substituting phenyl sulfonyl isocyanate for methane sulfonyl isocyanate in this procedure, the corresponding phenyl sulfoximide derivatives can also be made.

In addition the following sulfonimides can be prepared by substituting the other appropriately protected carboxylic acids of Examples 7, 10 and 14.

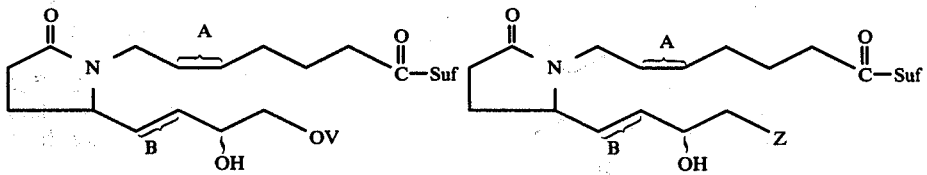

-continued

Suf = NHSO₂CH₃
NHSO₂Ph

V is defined in Example 10.
Z is defined in Example 7
A is a single or cis double bond
B is a single or trans double bond.

What is claimed is:
1. A compound of the structure

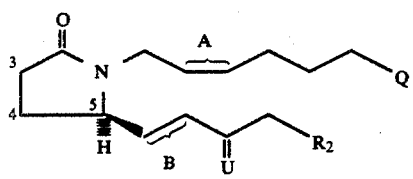

wherein:
Q is selected from the group consisting of

tetrazol-5-yl and

A is a single or cis double bond;
B is a single or trans double bond;
U is H⧸⧹OH HO⧸⧹H or H∼OH
$R_2$ is selected from the group consisting of α-thienyl, phenyl, phenoxy, monosubstituted phenyl and monosubstituted phenoxy, said substituents being selected from the group consisting of chloro, fluoro, phenyl, methoxy, trifluoromethyl and alkyl having from one to three carbon atoms;
$R_3$ is selected from the group consisting of hydrogen, alkyl having from one to five carbon atoms, phenyl and p-biphenyl;
$R_4$ is selected from the group consisting of

and —SO₂R₅, said R₅ being selected from the group consisting of phenyl and alkyl having from one to five carbon atoms;
or the alkali, alkaline earth and ammonium salts of those compounds having a carboxylate or tetrazol-5-yl group.
2. A compound of claim 1 wherein $R_2$ is phenyl, substituted phenyl or α-thienyl.
3. A compound of claim 1 wherein $R_2$ is phenoxy or substituted phenoxy.
4. A compound of claim 2 wherein Q is

5. A compound of claim 2 wherein Q is tetrazol-5-yl.
6. A compound of claim 2 wherein Q is

7. A compound of claim 3 wherein Q is

8. A compound of claim 3 wherein Q is tetrazol-5-yl.
9. A compound of claim 3 wherein Q is

10. The compound of claim 4 wherein A is a single bond, B is trans double bond, $R_2$ is phenyl, $R_3$ is hydrogen and U is H∼OH.
11. The compound of claim 4 wherein A is a single bond, B is a single bond, $R_2$ is phenyl, $R_3$ is hydrogen and U is H∼OH.
12. The compound of claim 7 wherein A is a single bond, B is a trans double bond, $R_2$ is phenoxy, $R_3$ is hydrogen and U is H∼OH.
13. A compound of the structure:

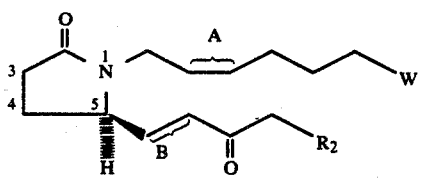

wherein:
W is selected from the group consisting of

tetrazol-5-yl, N-(acyloxymethyl)tetrazol-5-yl having from two to five carbon atoms in the acyloxy group, N-(phthalidyl)tetrazol-5-yl; and N-(tetrahydropyran-2-yl)-tetrazol-5-yl;
A is a single or cis double bond;
B is a single or trans double bond;
$R_2$ is selected from the group consisting of α-thienyl, phenyl, phenoxy, monosubstituted phenyl and monosubstituted phenoxy, said substituents being selected from the group consisting of chloro, fluoro, phenyl, methoxy, trifluoromethyl and alkyl having from one to three carbon atoms;
$R_3$ is selected from the group consisting of hydrogen, alkyl having from one to five carbon atoms, phenyl and p-biphenyl;
or the alkali, alkaline earth and ammonium salts of those compounds having a carboxylate or tetrazol-5-yl group.
14. A compound of the structure

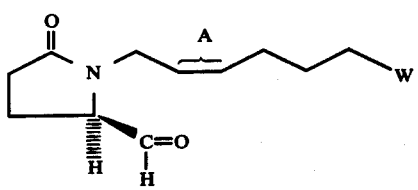
wherein:
A is a single or cis double bond;
W is selected from the group consisting of tetrazol-5-yl, N-(acyloxymethyl)tetrazol-5-yl, having from two to five carbon atoms in the acyloxy group,
N-(phthalidyl)tetrazol-5-yl and N-(tetrahydropyran-2-yl)tetrazol-5-yl.
15. A compound of the structure
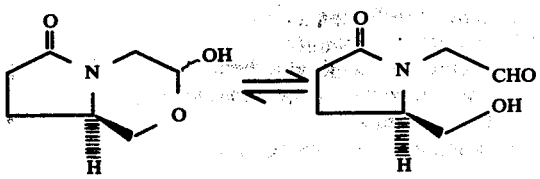
* * * * *